(12) United States Patent
Hickman

(10) Patent No.: US 9,092,833 B2
(45) Date of Patent: Jul. 28, 2015

(54) CLAIMING REAL ESTATE IN PANORAMIC OR 3D MAPPING ENVIRONMENTS FOR ADVERTISING

(75) Inventor: Ryan Hickman, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 13/486,431

(22) Filed: Jun. 1, 2012

(65) Prior Publication Data

US 2012/0246013 A1 Sep. 27, 2012

Related U.S. Application Data

(63) Continuation of application No. 12/168,695, filed on Jul. 7, 2008, now abandoned.

(51) Int. Cl.
*G06Q 30/00* (2012.01)
*G06Q 50/16* (2012.01)
(Continued)

(52) U.S. Cl.
CPC ............... *G06Q 50/16* (2013.01); *A61B 8/485* (2013.01); *G06Q 30/02* (2013.01); *G06Q 30/0261* (2013.01)

(58) Field of Classification Search
CPC ....... G06Q 30/02; G06Q 30/00; A61B 8/485; A61B 8/14; A61B 8/00; G01J 3/02; G01J 3/0224; G01J 3/10; G01N 2021/6417; G01N 21/6445; G01N 21/6452; G01N 21/6456; G01N 21/648; G01N 2201/126; G01N 27/82; G08G 1/123; G06K 9/34; G06K 9/03; G09G 5/00; G09G 5/08; G06F 9/44; G06F 17/50; G06F 17/30; H04N 7/173; H04N 5/74; H04N 5/225; H04B 17/00; H04B 10/08; H04M 1/66; G11C 8/00; G03B 41/00

USPC .................. 705/1.1, 14, 26, 86; 703/1; 707/6; 600/437, 459; 324/240; 398/25; 345/661; 340/995.1; 382/173; 365/233; 348/751; 455/411

See application file for complete search history.

(56) References Cited

U.S. PATENT DOCUMENTS 7,777,648 B2   8/2010 Smith et al.
7,974,853 B1 *  7/2011 Zimmerman .................. 705/1.1
(Continued)

FOREIGN PATENT DOCUMENTS

JP  11-296540 A   10/1999
KR  2000-0072571 A  12/2000
(Continued)

OTHER PUBLICATIONS

International Preliminary Report on Patentability for PCT Application No. PCT|US2009/049700, mailed Jan. 20, 2011, 7 pages.
(Continued)

*Primary Examiner* — James Trammell
*Assistant Examiner* — Sanjeev Malhotra
(74) *Attorney, Agent, or Firm* — Fish & Richardson P.C.

(57) ABSTRACT

Techniques for identifying groups of features in an online geographic view of a real property and replacing and/or augmenting the groups of features with advertisement information are described. The techniques include providing a geographic view of a property within an online property management system, identifying a region of interest in the geographic view, analyzing the geographic view to locate one or more promotional features within the geographic view positioned upon a real property region, providing a user-selectable link associated with the region of interest in the geographic view, receiving a request for the region of interest in the geographic view via the user-selectable link, receiving data to alter at least one of the behavior or the appearance of the region of interest, storing the data in association with the geographic view, and updating the region of interest within the geographic view based upon the received data.

20 Claims, 12 Drawing Sheets

(51) Int. Cl.
  *A61B 8/08* (2006.01)
  *G06Q 30/02* (2012.01)

(56) References Cited

U.S. PATENT DOCUMENTS

| | | | |
|---|---|---|---|
| 2004/0045028 A1* | 3/2004 | Harris | 725/86 |
| 2005/0021387 A1 | 1/2005 | Gottfurcht | |
| 2005/0127908 A1* | 6/2005 | Schlicker et al. | 324/240 |
| 2005/0192779 A1* | 9/2005 | Mertins et al. | 703/1 |
| 2005/0203390 A1* | 9/2005 | Torp et al. | 600/437 |
| 2005/0273458 A1 | 12/2005 | Adams | |
| 2006/0241859 A1 | 10/2006 | Kimchi et al. | |
| 2006/0280364 A1* | 12/2006 | Ma et al. | 382/173 |
| 2007/0027765 A1* | 2/2007 | Collins et al. | 705/14 |
| 2007/0032726 A1* | 2/2007 | Osaka et al. | 600/459 |
| 2007/0091713 A1* | 4/2007 | Wang | 365/233 |
| 2007/0106566 A1* | 5/2007 | Ranin et al. | 705/26 |
| 2007/0210937 A1* | 9/2007 | Smith et al. | 340/995.1 |
| 2008/0030628 A1* | 2/2008 | Lundquist et al. | 348/751 |
| 2008/0086356 A1 | 4/2008 | Glassman et al. | |
| 2008/0109433 A1* | 5/2008 | Rose | 707/6 |
| 2008/0119167 A1* | 5/2008 | Rao | 455/411 |
| 2008/0126206 A1 | 5/2008 | Jarrell | |
| 2008/0198178 A1* | 8/2008 | Julin et al. | 345/661 |
| 2008/0212960 A1* | 9/2008 | Lundquist et al. | 398/25 |
| 2008/0215415 A1 | 9/2008 | Willms | |
| 2010/0004995 A1 | 1/2010 | Hickman | |
| 2010/0034466 A1 | 2/2010 | Jing et al. | |

FOREIGN PATENT DOCUMENTS

| | | |
|---|---|---|
| KR | 10-2001-0105634 A | 11/2001 |
| KR | 2003-0069950 A | 8/2003 |
| KR | 10-2005-0094557 A | 9/2005 |
| KR | 10-2005-0116963 A | 12/2005 |

OTHER PUBLICATIONS

International Search Report and Written Opinion for PCT Application No. PCT|US2009/053353 dated Feb. 24, 2010,14 pages.
International Preliminary Report on Patentability for PCT|US2009/053353, mailed Feb. 24, 2011, 9 pages.
Schmid, C., et al., "Evaluation ofInterest Point Detectors", International Journal of Computer Vision, 37(2), 151-172, 2000, 22 pages.
International Search Report and Written Opinion for corresponding International Application No. PCT|US2009/049700, mailed Jan. 29, 2010.
Office Action issued in U.S. Appl. No. 12/168,695 on Jan. 20, 2012, 14 pages.
Chinese Office Action issued in Chinese Application No. 200980134696.4 on Mar. 28, 2012, English Translation only, 7 pages.
Office Action issued in U.S. Appl. No. 12/025,862 on Oct. 6, 2010, 8 pages.
Office Action issued in U.S. Appl. No. 12/025,862 on Apr. 4, 2011, 8 pages.
Office Action issued in U.S. Appl. No. 12/025,862 on Sep. 29, 2011, 9 pages.
Office Action issued in U.S. Appl. No. 12/025,862 on Apr. 12, 2012, 8 pages.
Office Action issued in U.S. Appl. No. 12/025,862 on Sep. 17, 2012, 7 pages.
Office Action issued in U.S. Appl. No. 12/025,862 on Mar. 15, 2013, 7 pages.
Office Action issued in U.S. Appl. No. 12/025,862 on Oct. 1, 2013, 8 pages.
Office Action issued in U.S. Appl. No. 12/025,862 on Apr. 9, 2014, 9 pages.
Office Action issued in Australian Application No. 2009268765 on Sep. 11, 2014, 4 pages.

* cited by examiner

FIG. 5

CLAIMING REAL ESTATE IN PANORAMIC OR 3D MAPPING ENVIRONMENTS FOR ADVERTISING

CROSS-REFERENCE TO RELATED APPLICATION

This application is a continuation of U.S. patent application Ser. No. 12/168,695, filed on Jul. 7, 2008, which is herein incorporated by reference in its entirety.

TECHNICAL FIELD

This disclosure is generally related to online advertising.

BACKGROUND

Interactive media (e.g., the Internet) may help improve the targeting of advertisements ("ads") to receptive audiences. Ads can be presented as banner ads, sets of one or more text boxes, video ads, audio ads, and the like. For example, some websites provide information search functionality that is based on key words entered by the user seeking information. This user query can be an indicator of the type of information of interest to the user. By comparing the user query to a list of key words specified by an advertiser, it is possible to provide targeted ads to the user.

Another form of online advertising is ad syndication, which allows advertisers to extend their marketing reach by distributing contextual ads to additional partners. For example, third party online publishers can place an advertiser's text or image ads within or alongside desired publisher content to motivate potential customers to seek additional information (e.g., navigate to the advertiser's website, etc.).

In contextual advertising systems, ads are selected and served by automated systems based on the content displayed to the user in, for example, a browser window. The displayed content is analyzed to determine the "context" of the information (e.g., the main topic) so that ads that best match the context can be targeted to the content display. In contextual advertising systems, once the context of a content display is matched to a set of potential advertisements for display, an auction mechanism is used to select one or more potential advertisements to actually appear on the page.

Using interactive web mapping services, users can navigate a map based upon an input location. For example, a map of a street address could be modified in granularity (e.g., zoom in and out) or navigated directionally (e.g., pan to the north, east, south, west, etc.). Some web mapping services also provide the service of requesting driving directions between locations.

An additional capability provided by some web mapping services can include a panoramic view of the street location. For example, a user could view and/or navigate street-level images within an interactive web mapping service. The street-level images, for example, can be captured by a camera attached to a vehicle. The street level images can be navigated in a manner similar to the web mapping services, with granularity and directional navigation options.

SUMMARY

According to one general aspect, a computer implemented method for managing one or more real property regions includes providing a geographic view of a property within an online property management system, identifying a region of interest in the geographic view including at least a portion of a real property region, analyzing the geographic view to locate one or more promotional features within the geographic view positioned upon a real property region, providing a user-selectable link associated with the region of interest in the geographic view, receiving a request for the region of interest in the geographic view via the user-selectable link, receiving data to alter at least one of the behavior or the appearance of the region of interest, storing the data in association with the geographic view, and updating the region of interest within the geographic view based upon the received data.

Implementations may include one or more of the following features. For example, receiving the data includes receiving one or more images. Updating the region of interest based upon the received data includes replacing the region of interest with the image provided within the received data. The one or more promotional features include one or more of signs, posters, banners, or billboards.

In another general aspect, a computer-readable medium with computer-executable instructions stored thereon performs the method of providing a geographic view of a property within an online property management system, identifying a region of interest in the geographic view including at least a portion of a real property region, analyzing the geographic view to locate one or more promotional features within the geographic view corresponding to a real property region, providing a user-selectable link associated with the region of interest in the geographic view, receiving a request for the region of interest in the geographic view via the user-selectable link, receiving data to alter at least one of the behavior or the appearance of the region of interest, storing the data in association with the geographic view, and updating the region of interest within the geographic view based upon the received data.

Implementations may include one or more of the following features. For example, receiving the data includes receiving one or more images. Updating the region of interest based upon the received data includes replacing the region of interest with the image provided within the received data. The one or more promotional features include one or more of signs, posters, banners, or billboards.

In another general aspect, a computer implemented method for managing one or more real property regions includes presenting a geographic view within an online property management system, the geographic view having discrete regions of interest, receiving input identifying one of the discrete regions of interest, analyzing the identified discrete region of interest within the geographic view, verifying that the identified discrete region of interest can be modified by the user by authenticating that the identified discrete region of interest lies upon a real property region, and storing the location of the identified discrete region of interest in association with the geographic view.

Implementations may include one or more of the following features. For example, receiving data to alter at least one of the behavior or the appearance of the identified discrete region of interest. Receiving the data includes receiving one or more images. Storing the received data and updating the identified discrete region of interest based upon the received data. Verifying that the identified discrete region of interest can be modified by the user includes authenticating that the identified discrete region of interest lies within a real property region belonging to the user. Receiving data describing the identified discrete region of interest. Receiving data describing the identified discrete region of interest includes receiving data regarding the availability of the identified discrete region of interest to public bidding. The received data includes information regarding a business or residence.

In another general aspect, a computer-readable medium with computer-executable instructions stored thereon performs the method of presenting a geographic view within an online property management system having one or more discrete regions of interest, receiving input identifying a discrete region of interest, analyzing the identified discrete region of interest within the geographic view, verifying that the identified discrete region of interest can be modified by the user by authenticating that the identified discrete region of interest lies upon a real property region, and storing the location of the identified discrete region of interest in association with the geographic view.

Implementations may include one or more of the following features. For example, performing the additional step of receiving data to alter the identified discrete region of interest. Performing the additional step of receiving data describing the identified discrete region of interest. Receiving data describing the identified discrete region of interest includes receiving data regarding the availability of the identified discrete region of interest to public bidding.

In another general aspect, a computer implemented method for managing one or more real property regions within an online property management system method includes receiving data including an image, locating one or more available discrete regions of interest within one or more geographic views having a similar size ratio to the received image, presenting the one or more available discrete regions of interest, and receiving a bid for the one or more available discrete regions of interest.

Implementations may include one or more of the following features. For example, receiving a geographic region for use in locating the one or more available discrete regions of interest. Presenting a suggested bid for the one or more available discrete regions of interest.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5 is a screen shot of an example user interface for associating one or more advertisements with an online property.

Like reference symbols in the various drawings indicate like elements.

DETAILED DESCRIPTION

Figure 1:
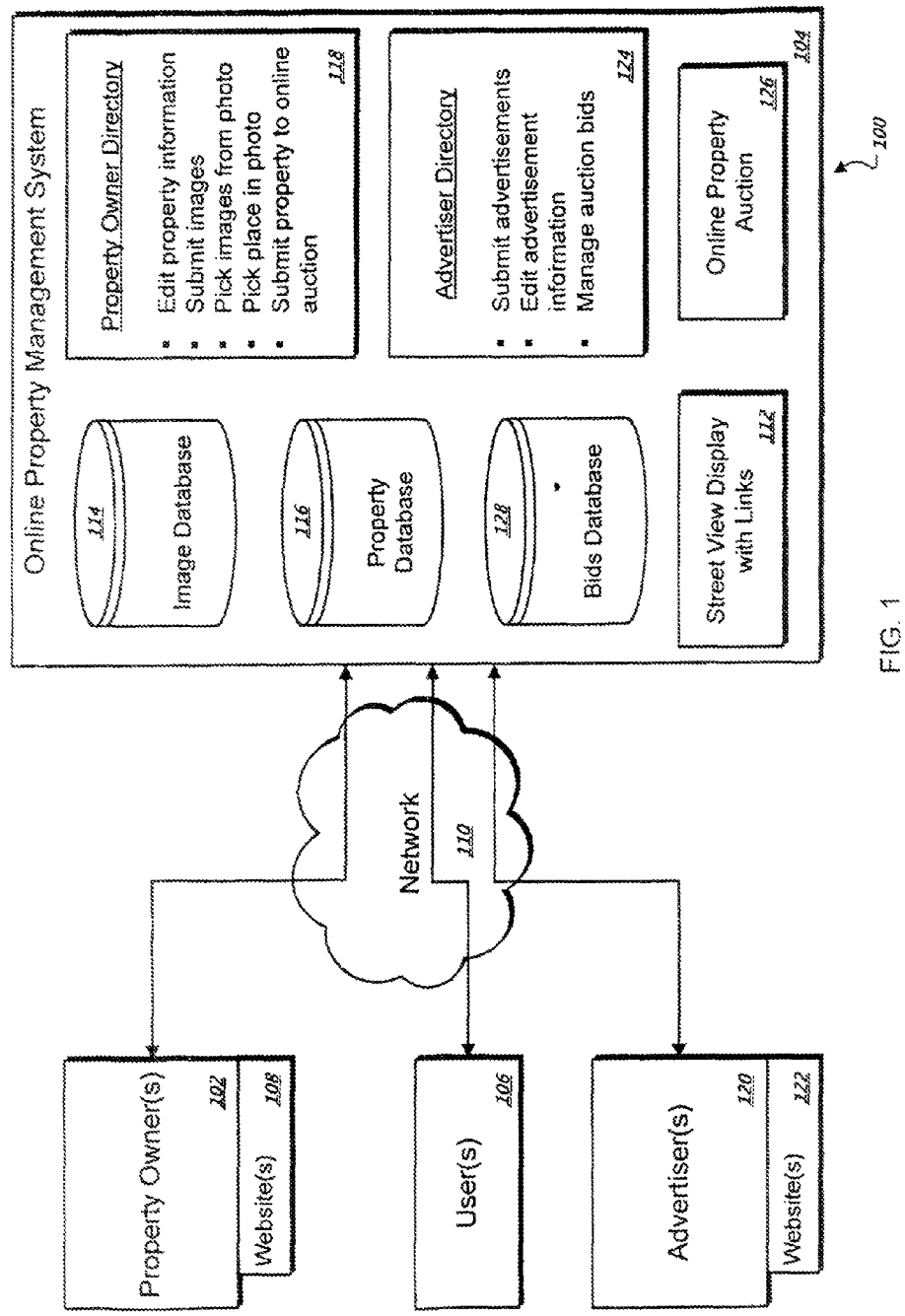
FIG. 1 illustrates an example of an environment 100 for implementing a virtual property management system.

FIG. 1 illustrates an example of an environment 100 for implementing a virtual property management system. One or more property owners 102 and/or advertisers 120 can directly or indirectly enter, maintain, and track advertisement ("ad") information, including business details, in an online property management system 104. The ads may be in the form of graphical ads, such as banner ads, text only ads, image ads, audio ads, video ads, ads combining one or more of any such components, etc. The ads may also include embedded information, such as hot-links, meta-information, and/or machine executable instructions. One or more users 106 may submit requests for virtual property information to the online property management system 104. The online property management system 104 responds by sending one or more images, including property advertisement information, to the requesting user 106. Users can include publishers which publish content (e.g., Internet website content). A computer network 110, such as a local area network (LAN), wide area network (WAN), the Internet, or a combination thereof, connects the property owners 102, the advertisers 120, the online property management system 104, and the users 106.

The online property management system 104 includes a street view display server 112 which can provide the user 106 with an image of a geographic location embedded and/or hot linked with advertisement information. The images available through the street view display server 112 can be used to provide the user 106 with mapping and/or driving directions information. For example, through interfacing with a Global Positioning System (GPS) navigational device, the user 106 can receive photographic images from the street view display server 112, providing the user 106 with a photographic image of the present location or a desired destination. The images are stored within an image database 114.

The online property management system 104 provides the property owners 102 with access to updating a property owner directory 118. In one example, the property owners 102 can access the property owner directory 118 to edit property information. The property information can include, for example, the name of the business located at the property, property address, telephone number, business hours, universal resource locator (URL) of a website 108 associated with the property, current promotional information (e.g., coupon, discount, etc.), email address of the property owner 102, a description of the business, a business category, or driving directions to the property location. The property information can be stored within a property database 116.

The property owners 102 can use the property owner directory 118 to upload images to the image database 114 within the online property management system 104. The image database 114 contains images which can be recognized as groups of features within a photographic image such as an image of a city block. For example, a car has a set of features including features composing the grill, tires, headlamps, hood, bumpers, windshield, mirrors, doors, windows, trunk, etc.

Groups of features, also described as a region of interest (ROI), can be selected from within a geographic photo display (e.g., by hand, through digital photographic recognition means, etc.) and added to the image database 114.

In some implementations, the property owner 102 can select an ROI within a panoramic image which includes an image of the property. For example, corporate logos, brick and mortar store signs, window posters, banner displays, marquis displays, and sandwich boards associated with the property can be stored within the image database 114. In some implementations, the location and dimension of the ROI as found within, for example, a panoramic image can be stored within the image database 114 or the property database 116.

An image uploaded by the property owner 102 can be designated to replace an ROI within a panoramic image. For example, the panoramic image of the property may include promotional images (e.g., window posters, marquis text, banners, etc.) referring to outdated promotions (e.g., Fall clearance sale). The property owner 102 can upload an image containing recent information (e.g., Spring shoe sale) to overlay the ROI which displays the outdated promotion.

The online property management system 104, in some implementations, can also provide the property owners 102 with the capability of offering one or more regions of interest within an associated property to bidding. For example, the property owner 102 of a billboard can designate (e.g., through the property owner directory 118) that the ROI describing the billboard within a panoramic image be provided for public bidding. The properties available for bidding can be stored within the property database 116. One or more advertisers 120 or other property owners 102, for example, can bid on overlaying the billboard defined by the ROI with an ad image. In some implementations, promotional features located within public areas (e.g., banners or posters identified within public property such as a town square) can also be made available for bidding. An online property auction server 126 can facilitate the bidding on property regions. A bids database 128 stores the bids and other advertisement information associated with each advertiser 120.

Within an advertiser directory 124, the advertisers 120 can, for example, edit advertisement information (e.g., select an advertisement category, limit the advertisement placement to a geographic region for targeting, associate a website 122 with one or more advertisements, etc.), submit advertisements to the online property management system 104 (e.g., into the image database 114), and manage online property bids.

In some implementations, the users 106 can request geographic views (e.g., city block, historical landmark, image of a strip mall, current traffic conditions on a segment of highway, etc.) from the online property management system 104. For example, the user 106 can request a street view in relation to visual driving directions. The street view display server 112 combines the requested content with one or more of the ad images provided by the property owners 102 and/or the advertisers 120. The street view display server 112 can additionally embed the requested content (e.g., using hot-links, etc.) with property information provided by the property owners 102.

The street view display server 112 compares photographic regions of interest with property owner-designated regions of interest stored within the image database 114 or the property database 116. If one or more property owners 102 have designated regions of interest within the requested image, the street view display server 112 can locate an ad image within the image database 114 and overlay the region of interest with the associated ad image. Applying an advertisement to a region of interest within a geographic view can include, in some implementations, creating a selectable region within the geographic view. The combined image content and advertisement content (e.g., overlaid ad images, hot-linked image regions, etc.) can be sent to the user 106 for presentation in a viewer (e.g., a web browser, a mobile device, a vehicle navigation device, or other content display system).

In some implementations, selecting a hot-linked region or embedded ad can provide the user with navigation to the property owner's website 108 or the advertiser's website 122. One or more property owners 102 and/or advertisers 120 can be associated with one or more websites 108, 122. For example, the property owner 102 can promote an Internet-based business, a brick and mortar business, or a business which has both an Internet presence and brick and mortar establishments.

As can be appreciated from the foregoing, the online property management system 104 can serve users 106, such as individual electronic devices, web publishers, content servers and search services. The online property management system 104 permits serving of ads targeted to regions of interest located within geographic displays. For example, a network or inter-network may include an online property management system serving geographic photos with in-line targeted ads in response to requests from a map and/or driving directions service. In some implementations, the user 106 provides the online property management system 104 with an addressing means (e.g., street address, GPS coordinates, etc.) for image selection. In response, the online property management system 104 coordinates a street view display of the address received with inline advertising and/or embedded advertising links targeted to one or more regions of interest recognized within the street view display. The street view display server 112 contains geographic display images which have already been reviewed, either electronically or by hand, and matched with groups of local features, the group being located within a region of interest. The photographic coordinates of the region of interest, for example, can match a region of interest designated by the property owner 102 for ad overlay. Advertisements are coordinated with the recognized feature groups and compiled within the street view display which is returned to the user 106.

Figure 2:
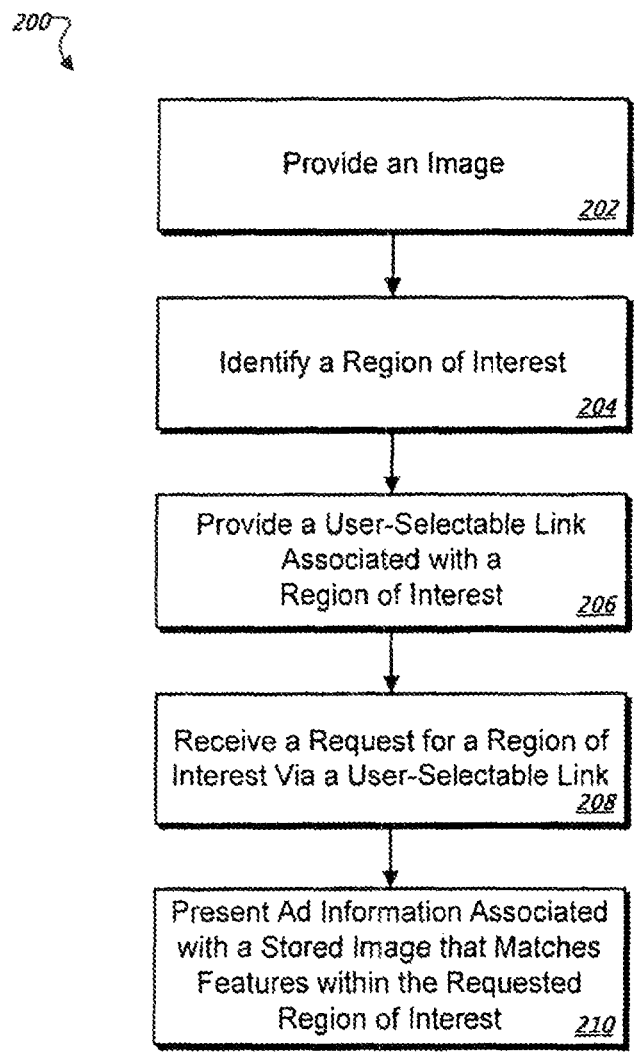
FIG. 2 is a flow diagram of an example image based ad targeting process.

FIG. 2 is a flow diagram of an example image based ad targeting process 200. The steps of process 200 do not have to occur in a specific order and at least some steps can occur in parallel. The ad targeting process 200 begins with providing an image (202). The image can be, for example, a geographic display image provided to the street view display server 122 (as shown in FIG. 1). The image is retrieved from the image database 114 in response to a request from the user 106 for a particular geographic location. For example, a user connected to the online property management system 104 via the network 110 can request a geographic display corresponding to a particular region (e.g., GPS coordinates, street address, etc.). The street view display server 112, for example, can retrieve the geographic display image associated with the requested region from the image database 114.

One or more regions of interest are identified within the image (204). Local features are portions or sections of the image file that are visually distinguishable. The detection of local features consists of two steps: interest point detection and feature generation. Interest point detection addresses the problem of finding visually salient, yet stable, points on images (e.g., the edge and corner of an object, etc.). Common algorithms include the Difference of Gaussian (DoG) approach, or the Laplacian of Gaussian (LoG) approach, which are described in C. Schmid, R. Mohrand and C. Bauckhage, Evaluation of Interest Point Detectors, Int'l Journal of Computer Vision, 37(2), 151-172, 2000 (http://perception.inrialpes.fr/Publications/2000/SMB00), which is incorporated herein by reference in its entirety. Once an interest point is detected, the second step, generally, is to generate features around the interest point. An exemplary approach to generating features around the interest point includes an orientation histogram. Upon identification of one or more of the local features, the group of local features, also referred to as the region of interest, can be compared with a physical property location (e.g., using information contained within the property database 116). For example, the outlines of a building such as a coffee shop can be identified. The property database 116 may contain coordinates (e.g., GPS coordinates) or other information matching the property to a property owner.

A user-selectable link is provided in relation to the region of interest (206). The link can be associated with a property owner, for example the property owner which owns the physical property portrayed. The link can alternatively be associated with an advertiser or a property owner which placed the highest bid on the image recognized within the region of interest (e.g., poster, billboard, banner, etc.). Any portion of the geographic display image in which the region of interest is located can be selectable (e.g., hot-linked). For example, the image of the coffee shop can be hot-linked to an advertisement for the coffee shop. In other examples, the coffee shop logo can be hot-linked to menu information, customer reviews, store hours, and/or other pertinent information. In some implementations, the property owner identifies a region of interest (e.g., the coffee shop sign and/or the coffee shop logo within the sign) for hot-linking ad information. In some implementations, user-selectable links are visually indicated. For example, a user-selectable region can be outlined, highlighted, or rendered in a brighter or shaded manner as compared to the remainder of the image. A user-selectable text link can be underlined, in bold, etc.

A request is received via a user-selectable link for information regarding a region of interest (step 208). For example, a user touches, clicks on, or otherwise provides input to the device on which the hot-link is displayed to receive further information in regard to the region of interest. For example, the user could select the coffee shop logo within a geographic view of a street. Selection of the hot-link navigates the user to content provided by the online property management system 104. The online property management system 104 coordinates the presentation of information associated with user-selectable links. In other implementations, the link navigates the user to the property owner 102 (e.g., a property owner's website 108) or the advertiser 120 (e.g., an advertiser's website 122).

Information associated with the selected region of interest is presented to the user (step 210). The information replaces the display of a portion of the image. For example, the information can be presented within an upper region of the image, presented in place of the entire image, etc. Alternatively, the information can be presented beneath the image, alongside the image, or in a separate display region from the image (e.g., pop-up window). The information can include an advertisement, hours of operation, menu information, customer reviews or ratings, or other information that is pertinent to the region of interest and/or the general location portrayed within the geographic display image. For example, an advertisement for the coffee shop associated with the coffee shop logo can be presented to the user upon selection of the coffee shop logo feature within the image.

Different types of information can be provided within the same selectable link. For example, a mouse-over, right click, etc. of a region can provide a first grouping of information. The first grouping of information can contain options for obtaining additional information. For example, a drop-down menu could be displayed, offering a product listing, customer reviews, and/or a discount offer for the coffee shop associated with the user-selectable logo. Selection of one of the options from the first grouping of information can provide the user with a second display of information associated with the feature (e.g., menu, coupon code, hours, etc.). Other levels of presentation are possible.

Figure 3:
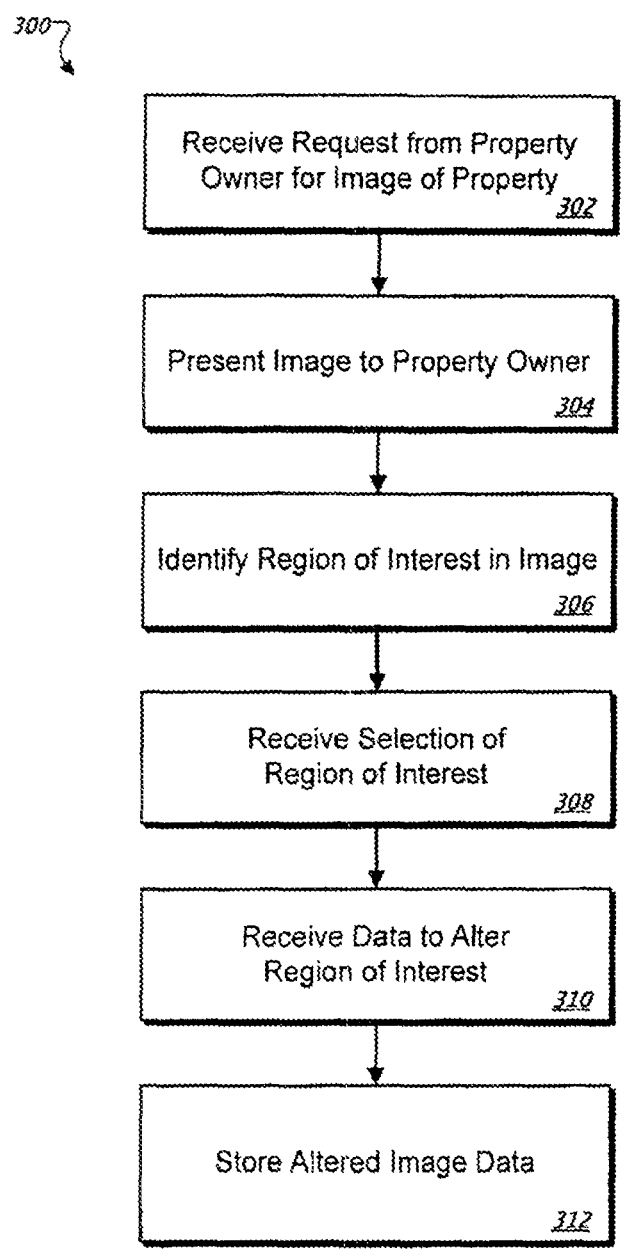
FIG. 3 is a flow diagram of an example process for altering the image of an online property.

FIG. 3 is a flow diagram of an example process 300 for altering the image of an online property. The steps of process 300 do not have to occur in a specific order and at least some steps can occur in parallel. The process 300 begins with receiving a request from a property owner for an image of a property (302). The property owner, in some implementations, goes through a verification procedure to obtain access to the online management of one or more physical properties. For example, the property owner may input verification information to the online property management system 104 (shown in FIG. 1) to gain access to the property. If the property owner owns multiple properties, the property owner may select, for example, from a list of addresses to designate a specific property.

The property image is presented to the property owner (304). In some implementations, the property image is contained within a panoramic view (e.g., a view of a city block). For example, the street view display server 112 can provide the property owner 102 with an image from the image database 114.

One or more regions of interest are identified within the image (306). In some implementations, the section of the image picturing property owned by the property owner is first identified. For example, the outline of a gas station property can be identified. Within the identified property, in some implementations, promotional features (e.g., posters, signs, billboards, banners, sandwich boards, etc.) can be identified as discrete regions of interest. Each ROI associated with a promotional feature, in some implementations, can be identified by a visible mark (e.g., outline, highlight, shadow, etc.). For example, the marquis and each individual window poster displayed on a theater property can be individually identified as regions of interest.

Selection of a region of interest is received (308). In some implementations, the property owner 102 can touch, click on, or otherwise provide input to the device on which the ROI is displayed to receive further information in regard to the ROI. The property owner 102 can alternatively, in some implementations, select an ROI within the image which was not previously identified. For example, the property owner 102 can drag a box across a window of the property displayed to designate an ROI.

Data is received to alter the selected region of interest (310). In some implementations, the property owner 102 uploads an image to the online property management system 104 to replace the identified ROI. For example, if the property owner 102 of a movie theater selected a window poster regarding a holiday movie, the property owner 102 could replace the region of the poster with an image advertising a new movie release. The property owner 102 could, in some implementations, associate the ROI with a hot link to promotional information. For example, the property owner 102 could select the sign on the store front for a hot link to the property owner's website 108. In another example, the property owner 102 could create an advertisement such as a coupon and hot link it into the ROI.

The altered image data is stored (312). In some implementations, the uploaded image is stored within the image database 114. If property information has been modified (e.g., adding a promotion such as a coupon, modifying business hours, etc.), the property database 116 is updated to reflect the new information. The location(s) of the modified region(s) of interest within the main image, in some implementations, are also stored within the image database 114 or the property database 116.

In some implementations, the presented image is updated to reflect the modifications within the property owner's view. In some implementations, the property owner 102 can make more than one modification within the same presented image. For example, the property owner 102 could select both a window poster ROI and a rooftop billboard ROI for modification. In some implementations, the property owner 102 can upload multiple images to a single ROI. For example, the ROI could switch between two uploaded images upon mouseover, on a set schedule (e.g., every 10 seconds), etc. Other implementations are possible.

Figure 4:
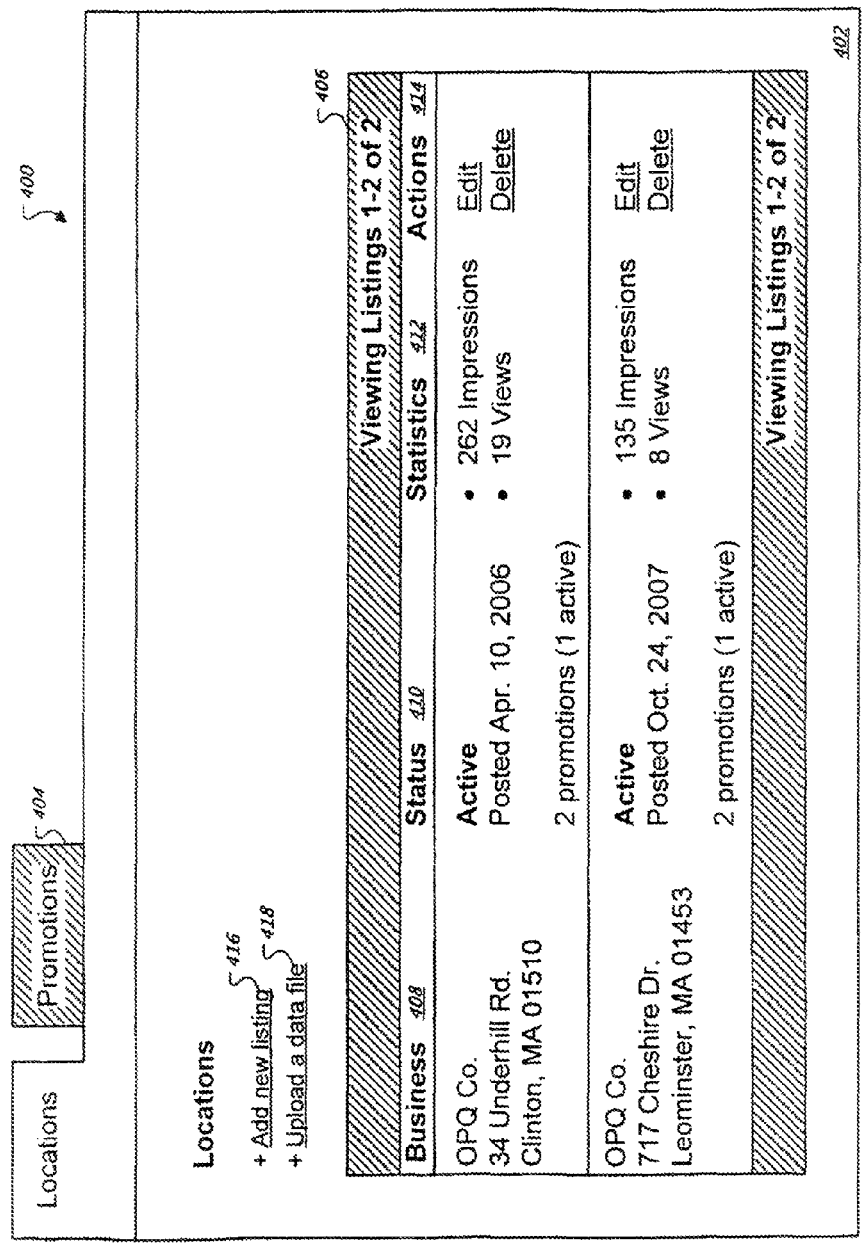
FIG. 4 is a screen shot of an example user interface for managing online property information.

FIG. 4 is a screen shot of an example user interface 400 for managing online property information. For example, the user interface 400 could be provided by the property owner directory 118 of FIG. 1 for managing property information. A locations tab 402 is active, providing the property owner with an interface for managing property locations. A promotions tab 404 is also available for review.

Two business locations are visible within the location listing box 406. A business column 408 lists the addresses of the businesses. In some implementations, in addition to businesses, locations can include any type of property, such as parks, statues, public squares, billboards, etc. A property owner can be associated with any number of properties.

A status column 410 lists an active status for each location. In some implementations, an active status means that the location is hot-linked into a geographic image (e.g., an image provided by the street view display server 112 of FIG. 1). The status column 410 also lists a posted date for each business 408. The posted date, for example, could be the date when the property owner first linked property information to the geographic image. Promotions are also listed within the status column 410. For example, the property owner could have added promotions (e.g., hot-linked coupons, etc.) to the business information using the promotions tab 404.

A statistics column 412 lists the number of impressions and views that each business 408 has received. In some implementations, the numbers of impressions and views relate to statistics since the posting date listed within the status column 410. Impressions, for example, can relate to the number of times the image including the business 408 has been requested by a user. The views statistic, for example, could be the number of times a user has requested business information (e.g., using a hot-link) from within the provided image.

An actions column 414 provides the property owner with the capability of editing or deleting each individual business listing 408. A property owner may choose to delete a business listing, in some examples, if the business has closed down or been sold.

Within the locations tab 402, the property owner is also presented with the options of adding a new listing 416 and uploading a data file 418. Selecting add a new listing 416, for example, can involve a further user interface where business information such as address and promotional information can be inputted. Selecting upload a data file 418, for example, can allow the property owner to upload pre-formatted information to edit or add a group of listings. For example, selecting upload a data file 418 can give the owner of a chain of restaurants the opportunity to upload information in bulk pertaining to the entire restaurant chain.

Figure 5:
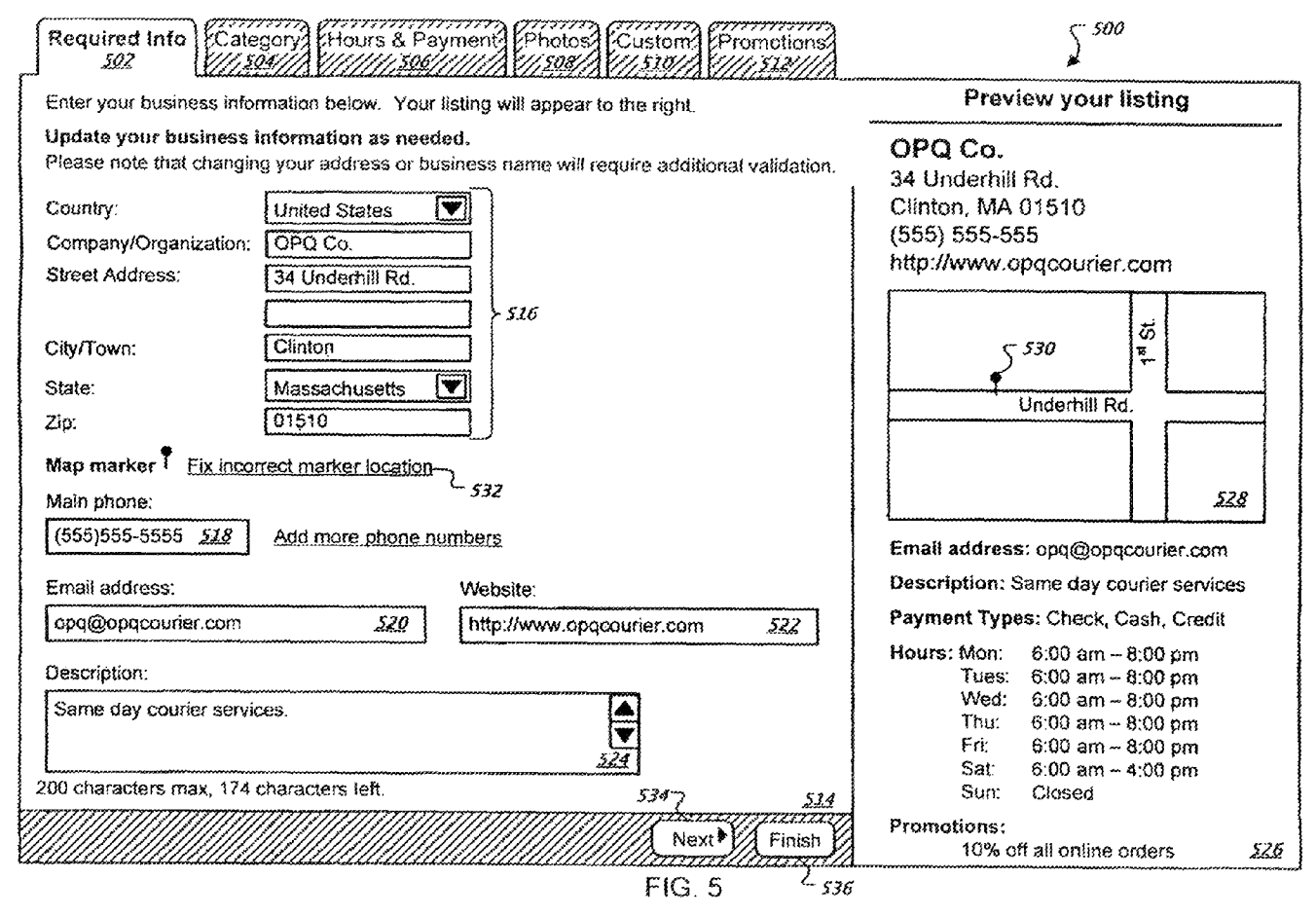

FIG. 5 is a screen shot of an example user interface 500 for associating advertisements with an online property. In some implementations, the user interface 500 is reached by selecting the edit option within the actions column 416 of the screen shot 400 in FIG. 4. A required info tab 502 is active. A category tab 504, an hours & payment tab 506, a photos tab 508, a custom tab 510, and a promotions tab 512 are also available within the user interface 500.

The required info tab 502 provides the property owner with the ability to enter or update basic business information. Within a data entry pane 514, the property owner is presented with data fields such as an address entry block 516, a phone number field 518, an email address field 520, and a website field 522. A description data entry box 524 allows the property owner to enter a brief description of the business, in this case "same day courier services".

A preview pane 526 illustrates to the property owner the business information entry. Included within the preview pane 526 is a map 528 of the business location. A map marker 530 illustrates to the viewer where the business is located within the map 528. By selecting a map marker hot link 532 within the data entry pane 514, the property owner can fix an incorrect map marker location.

A next button 534, when selected, can direct the property owner to the next information editing screen. For example, selection of the next button 534 from within the required info tab 502 can open the category tab 504. The category tab 504, in some implementations, can allow the property owner to select a business category and/or subcategory for listing. For example, the property owner could select a category "courier" for the OPQ Co. entry. In some implementations, more than one category can be selected (e.g., both restaurant and bakery).

The hours & payment tab 506 can provide the property owner with data entry for the business hours by day of the week and accepted payment types (e.g., cash, check, credit, etc.). The photos tab 508, in some implementations, can provide the property owner with the opportunity to upload images to replace regions of interest within a geographic photo display of the business. For example, using the photos tab 508, the property owner could upload one or more images to the image database 114 (as shown in FIG. 1) to overlay sections of a geographic image of the property provided by the street view display server 112.

The custom tab 510 can provide the property owner with customization options for modifying the listing (e.g., different fonts, layout, upload of logo image, etc.). The promotions tab 512 can present the property owner with the option of adding a coupon or promotional message to the business entry. When information from all desired tabs has been updated, the property owner can select a finish button 536 to exit the user interface 500.

Figure 6:
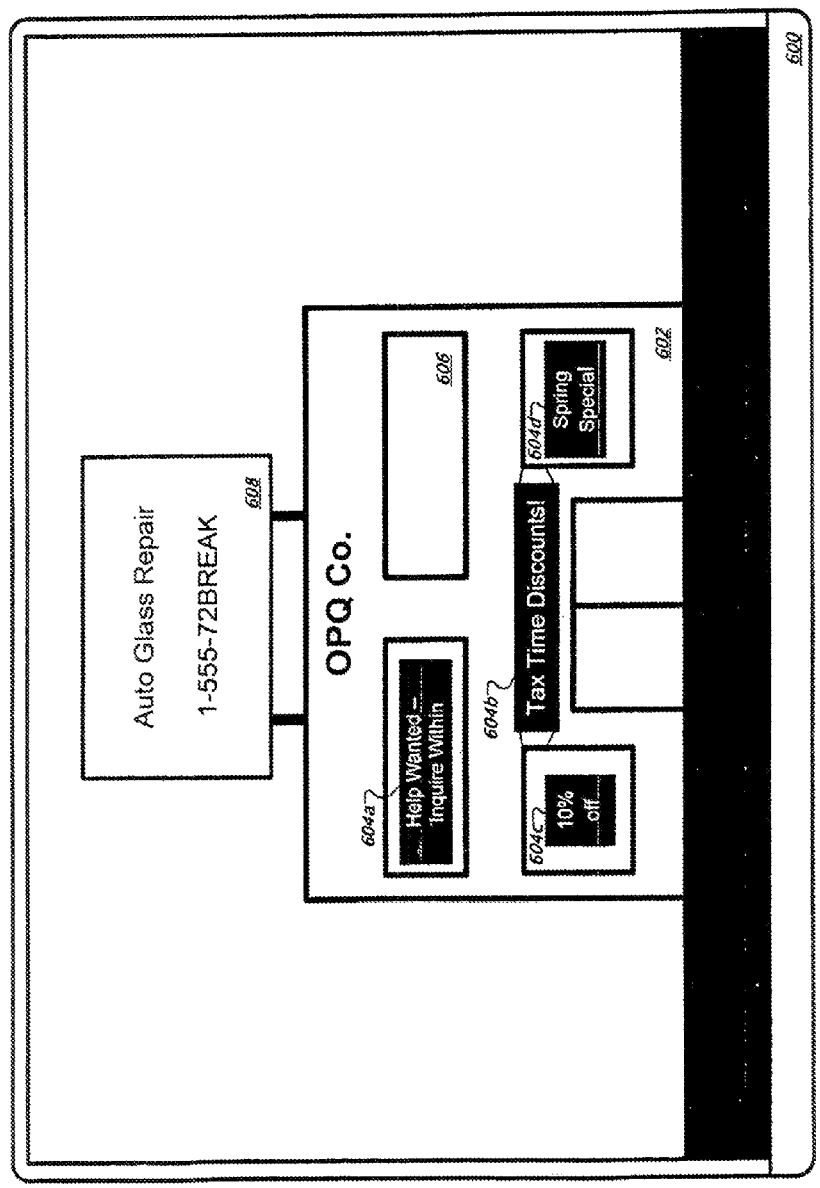
FIG. 6 is a screen shot of an example geographic image including a property.

FIG. 6 is a screen shot of an example geographic image 600 including a business property 602. The geographic image 600, for example, could be provided by the street view display server 112 from the online property management system 104 (as shown in FIG. 1). In some implementations, the property owner can access the geographic image 600 through the property owner directory 118 (as shown in FIG. 1) or the photos tab 508 of the user interface 500 (as shown in FIG. 5).

Within the business property 602, four promotional features 604, including a help wanted sign 604a, a promotional banner 604b, and window posters 604c, 604d are displayed.

In some implementations, the promotional features 604 are visually identified (e.g., highlight, shadow, outline, etc) with selectable hot-links. For example, the online property management system 104 could identify promotional features 604 within the business property 602 and present the promotional features 604 to the property owner for selection. The property owner, in some implementations, could select one or more promotional features 604 to associate with advertisements. For example, the property owner could upload one or more images to replace one or more regions of interest in which a promotional feature is located. The property owner, in some implementations, could instead or additionally select one or more promotional features to hot-link to advertisement information (e.g., coupon, business listing information, etc.).

In addition to the promotional features 604, in some implementations the property owner can select a region of interest which does not include a promotional feature. For example, the property owner could select the window 606 to associate with one or more advertisements (e.g., promotional image, hot-linked coupon, etc.). In some implementations, the online property management system 104 can accept any region of interest which is verified to be located within the property owner's property. For example, the property owner could drag a box across a section of the business property 602 to define a ROI.

The geographic image 600 also includes a billboard property 608. The billboard property can belong to the same property owner as the business property 602 or a second property owner. In some implementations, the billboard property 608 and/or the promotional features 604 can be offered to advertisers and/or other property owners for bidding. For example, the property owner of the billboard property 608 can submit the billboard property 608 to the online property auction server 126 (as shown in FIG. 1). Advertisers 120 can bid on placing advertisements upon the billboard property 608.

When a user views the geographic image 600, in some implementations, the user can select the business property 602, the billboard property 608, and/or the individual promotional features 604 to receive further advertising information. For example, the user 106 could request the geographic image 600 from the online property management system 104. The street view display server 112 could combine the geographic image 600 with promotional features and advertisement content provided by the property owner(s) of the business property 602 and/or the billboard property 608 or, alternatively, the advertiser(s) who bid on the billboard property promotional space and/or one or more of the promotional features 604. If the user 106 selects one or more hot-linked regions of interest within the geographic image 600 (e.g., the business property 602, the billboard property 608, and/or the promotional features 604), the online property management system 104 can navigate the user 106 to advertisement information (e.g., the website 108 of the property owner 102 or the website 122 of the advertiser 120).

Figure 7:
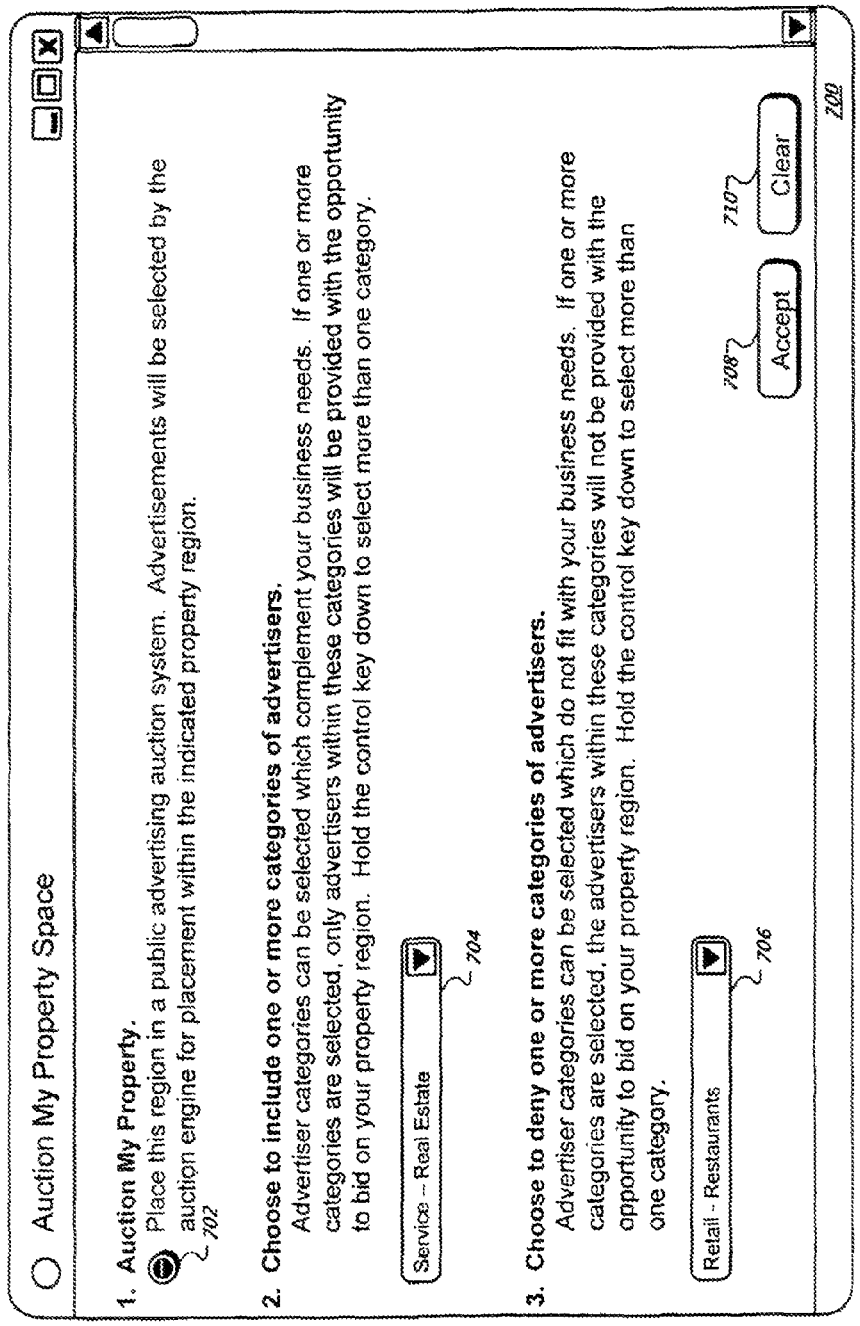
FIG. 7 is a screen shot of an example user interface for placing an online property in public auction.

FIG. 7 is a screen shot of an example user interface 700 for placing an online property in public auction. The user interface 700, for example, could be reached by selecting the billboard property 608 from within the geographic image 600 (as shown in FIG. 6). The property owner can submit a selected property region through the user interface 700 to a public auctioning system. Using the public auctioning system, advertisers can bid for the opportunity to place an advertisement upon the selected property region. The property owner can optionally choose to include and/or exclude categories of advertisers from bidding upon the selected property region. The information submitted through the user interface 700, for example, can be stored within the property owner directory 118 of the online property management system 104 (as shown in FIG. 1).

An "Auction My Property" radio button 702, when selected, places the selected property region (e.g., the billboard property region 608 as shown in FIG. 6) into a public advertising auction system such as the online property auction server 126 (as shown in FIG. 1). The auction system, for example, can select one or more advertisements for placement within the selected property region. The property owner, in some implementations, can receive a commission for advertisement placement.

A first category drop-down menu 704 includes a list of advertisement categories and/or subcategories (e.g., retail, retail-restaurants, service, service-real estate, etc.). The property owner can select one or more categories and/or subcategories using the drop-down menu 704. Selected categories and/or subcategories are used by the public advertising auction system to screen advertisements. For example, only advertisers and/or advertisements belonging to the selected categories can bid upon the selected property region. In some implementations, selection of one or more categories and/or subcategories within the drop-down menu 704 is optional.

A second category drop-down menu 706 includes a list of advertisement categories and/or subcategories. In some implementations, the drop-down menu 706 contains the same list of categories and/or subcategories as the drop-down menu 704. The drop-down menu 706 provides the property owner with the opportunity to select one or more categories and/or subcategories which will be barred from advertising within the selected property region. For example, a restaurant property owner can select the subcategory retail-restaurants within the drop-down menu 706 so that competing restaurants will not advertise within the selected property region. In some implementations, selection of one or more categories and/or subcategories within the drop-down menu 706 is optional.

Once the property owner has completed selections using the radio button 702, the drop down menu 704, and/or the drop-down menu 706, the property owner can activate an accept button 708 to submit the selections. In some implementations, activation of the accept button 708 closes the user interface 700. In other implementations, for example, selection of the accept button 708 can present the user with a summary screen listing the selections made within the user interface 700. The property owner can activate a clear button 710 to clear the selections made within the user interface 700.

Figure 8:
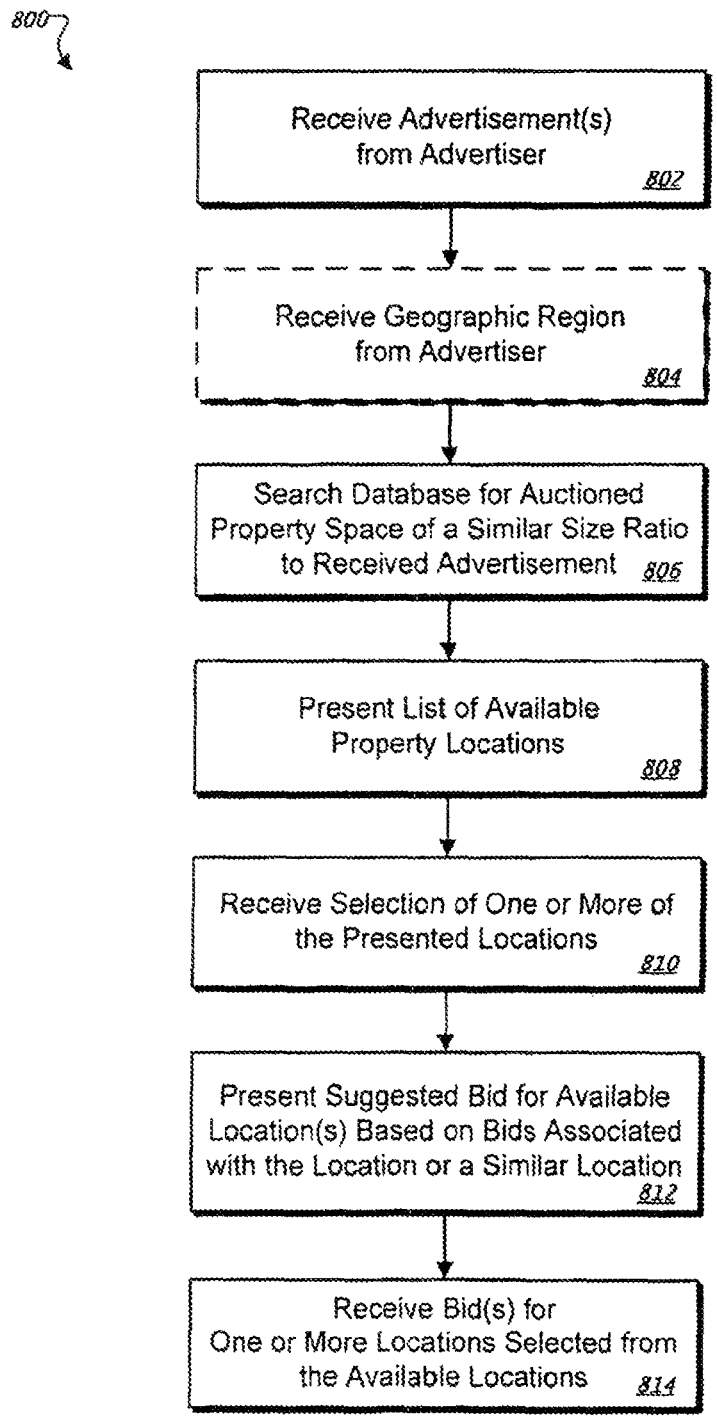
FIG. 8 is a flow diagram of an example process for bidding on advertisement placement in an online property auction system.

FIG. 8 is a flow diagram of an example process 800 for bidding on advertisement placement in an online property auction system. The steps of process 800 do not have to occur in a specific order and at least some steps can occur in parallel. The process 800, for example, can be implemented by the advertiser directory 124 of the online property management system 104 as shown in FIG. 1. The process 800 begins with receiving one or more advertisements from an advertiser (802). The advertisements, for example, can include graphical and/or multimedia information spanning one or more files and including any number of file types. The advertisements can be stored within the image database 114.

Optionally, a geographic region can also be received from the advertiser (804). In some implementations, the geographic region can be used to select a target area for presentation of the advertisement. For example, an advertisement for an upcoming concert can be presented within a geographic range (e.g., 25 miles) of the venue presenting the concert. In some examples, the geographic region can include an address, a zip code, a city, a state, a county, GPS coordinates, or other information describing a geographic region.

One or more databases are searched for auctioned property spaces of a similar size ratio to the received advertisements (806). For example, a graphic advertisement is received which has a certain dimensions (e.g., 200×400 pixels). The process 800 can search for property regions, for example within the property database 116 of FIG. 1, which have similar width to height dimensions. In some implementations, only properties within the specified geographic region are searched.

A list of available property locations is presented (808). In some implementations, a list of addresses is presented to the advertiser. The list of available property locations, in some implementations, can include an image of the property. For example, a thumbnail image of the location, optionally including an indication of the region available for advertisement placement (e.g., outline, highlight, etc.), can be presented to the advertiser.

Selection of one or more of the presented locations is received (810). In some implementations, the list of available property locations includes checkboxes or other user interface elements for selecting one or more of the presented locations.

A suggested bid is presented for each of the one or more selected locations (812). The suggested bid, in some examples, corresponds to an existing bid for the selected location or a bid for a similar location (e.g., similar presentation size, nearby geographical location, etc.). For example, the suggested bid can be located within the bids database 128 of FIG. 1. In addition to presenting a suggested bid, in some implementations, an input method is presented to the advertiser so that the advertiser can submit a bid.

Bids are received for one or more of the selected locations (814). For example, the advertiser can select the suggested bid or submit a new bid for each location of interest. In some implementations, if the advertiser submitted more than one advertisement, each bid is associated with a particular advertisement (e.g., advertisement "A" is 100×400 pixels while advertisement "B" is 600×400 pixels). The bid, in some implementations, leases the space to a particular advertiser and/or advertisement. In other implementations, the bid places the advertiser and/or advertisement in a list of advertisements associated with the property location. For example, two or more advertisers could be presented in the same advertising region in an alternating fashion. The received bid can be stored, for example, within the bids database 128. The bid information can be managed within the advertiser directory 124.

Although the process 800 is described as a series of steps, more or fewer steps can be involved in the process 800, and the steps can be executed in a different order. For example, presenting the list of available property locations (808) and presenting suggested bids (812) can be combined without the intermediate step of receiving the selection of one or more of the presented locations (810). In some implementations, the advertiser can navigate an online property system to locate available property space. For example, when the advertiser navigates to a property with a region available for bidding (e.g., using the street view display server 112 of FIG. 1), the advertiser can be alerted (e.g., highlighted region, "claim this property" link, etc.). The advertiser can select an available property region, and be presented with a suggested bid (812). In some implementations, the advertiser can provide additional criteria for selection of an advertisement space (e.g., availability dates, type of property, etc.).

Figure 9:
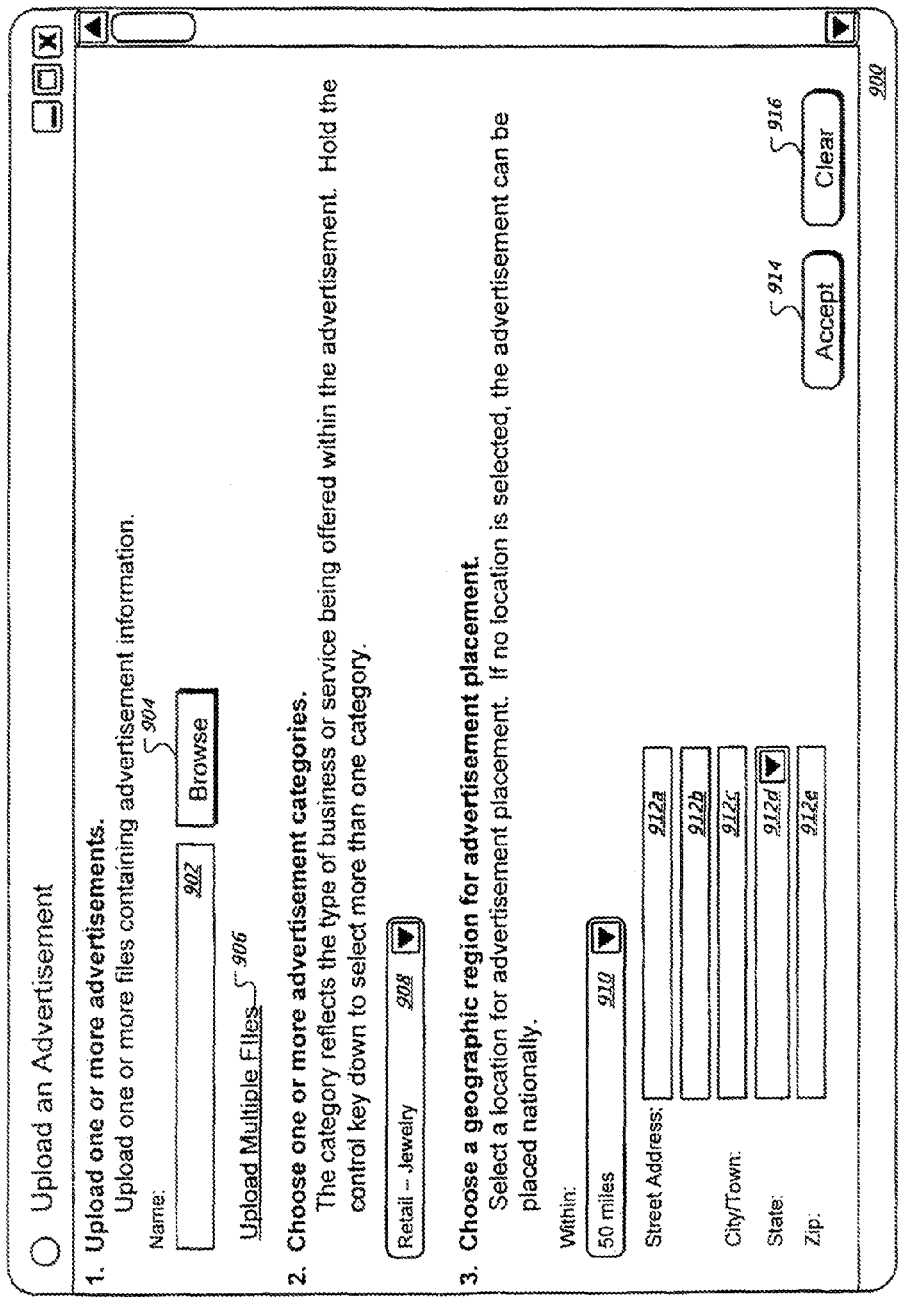
FIG. 9 is a screen shot of an example user interface for uploading advertisements into an online property auction system.

FIG. 9 is a screen shot of an example user interface 900 for uploading advertisements into an online property auction system. The user interface 900, for example, can be accessed by one or more advertisers 120 through the advertiser directory 124 to upload advertisements to the image database 114 of the online property management system 104 (as shown in FIG. 1). In addition to uploading advertisements, the advertiser is provided the opportunity to categorize the advertisement(s) by business type and/or limit the presentation of the advertisement(s) to a geographic region.

A file path text box 902 accepts the directory path to locate an advertisement file. A browse button 904, for example, can be used to navigate to the file location. Rather than uploading a single advertisement file, an upload multiple files link 906, when selected, provides the advertiser with a mechanism to bulk upload advertisement files.

A category drop-down menu 908 provides the advertiser with a selection of business categories and/or subcategories to associate with the uploaded advertisement(s). For example, the advertiser could associate one or more uploaded advertisements with the category "retail—jewelry". In some implementations, the category selection can be used to match the advertisement with an appropriate property placement through an online property auction. For example, the property owner (e.g., through user interface 700 as shown in FIG. 7) could select business categories to accept or deny for advertisement placement within a property region. In some implementations, the advertiser can select more than one category to associate with an advertisement (e.g., both "retail—jewelry" and "service—watch repair").

A distance drop-down menu 910 contains a selection of geographic ranges for advertisement placement. In coordination with a set of address input boxes 912 (e.g., a set of street address input boxes 912a and 912b, a city address box 912c, a state drop-down menu 912d, and a zip code input box 912e), the distance drop-down menu 910 can designate a radius in which the advertisement can be placed geographically. For example, an advertiser could choose to place an advertisement for a new museum within thirty miles of the address of the museum. Other possible geographic ranges, for example, include locations within a city, county, state, or zip code region. In some implementations, selection of a geographic region for placement is optional.

The advertiser can activate an accept button 914 to submit the selections made within the user interface 900. For example, selection of the accept button 914 can update the advertiser directory 124 with the new information and closes the user interface 900. The advertiser can instead activate a clear button 916 to clear all selections made within the user interface 900.

Figure 10:
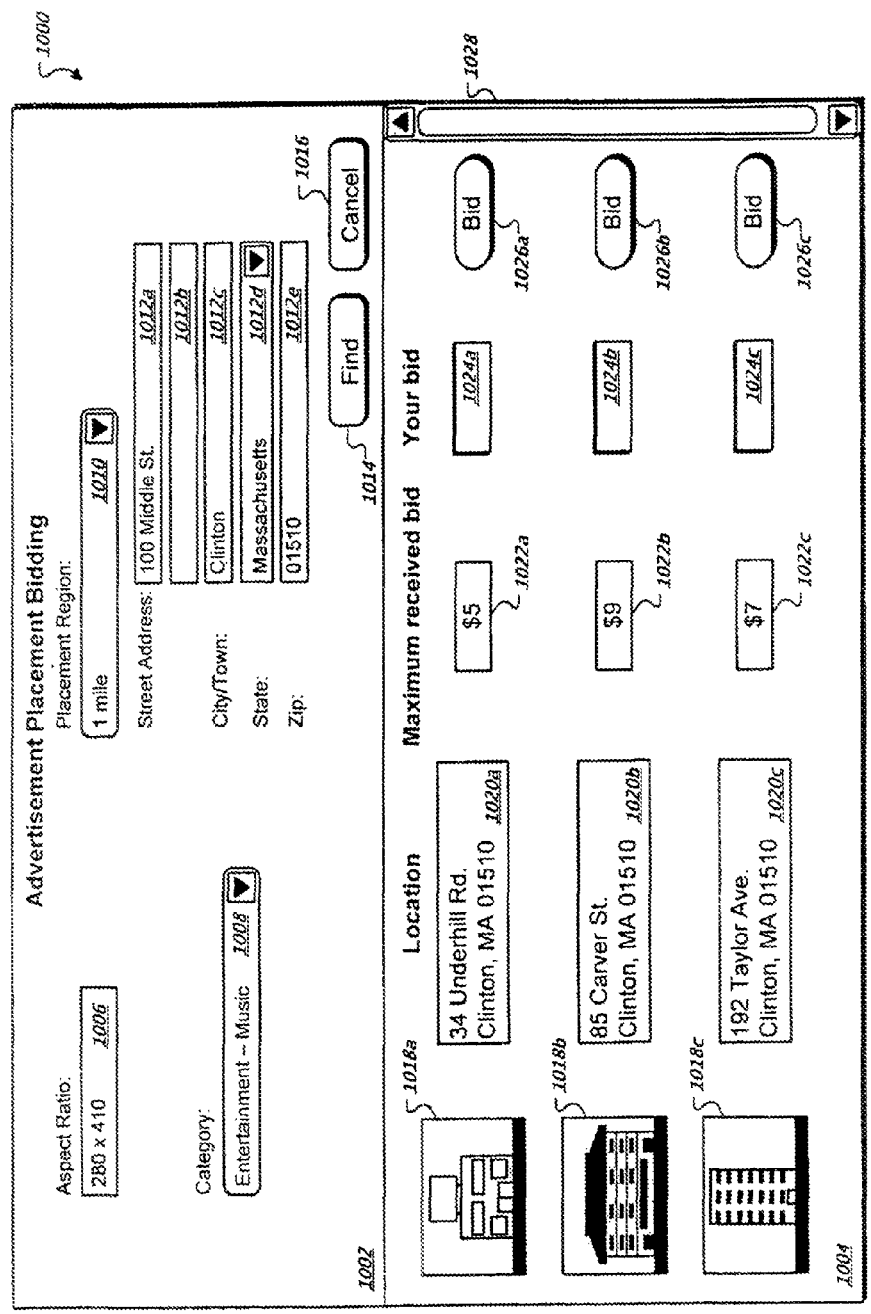
FIG. 10 is a screen shot of an example user interface for bidding on advertisement placement in an online property auction system.

FIG. 10 is a screen shot of an example user interface 1000 for bidding on advertisement placement in an online property auction system. The user interface 1000 includes an ad information pane 1002 for submitting information regarding one or more advertisements and an available property pane 1004 listing properties in which the advertisement(s) can be placed. The available property pane 1004 provides the advertiser with the option to place bids upon one or more available properties for ad placement. The user interface 1000, for example, can be accessed by advertisers 120 using the online property auction server 126 of FIG. 1.

The ad information pane 1002 includes an aspect ratio input box 1006. The aspect ratio refers to the height to width pixel ratio of the advertisement that the advertiser would like to place. In some implementations, the aspect ratio is automatically filled into the aspect ratio input box 1006, for example using an advertisement previously selected by the advertiser.

A category drop-down menu 1008 is available for the advertiser to categorize the advertisement into one or more types of business. For example, a choir concert advertisement can be classified as "entertainment—music".

A distance drop-down menu 1010 contains a selection of geographic ranges for advertisement placement. In coordination with a set of address input boxes 1012 (e.g., a set of street address input boxes 1012*a* and 1012*b*, a city address box 1012*c*, a state drop-down menu 1012*d*, and a zip code input box 1012*e*), the distance drop-down menu 1010 can designate a radius in which the advertisement can be placed geographically.

The advertiser can activate a cancel button 1016 to cancel the current bid request. For example, activation of the cancel button 1016 can clear the current selections within the aspect ratio input box 1006, the category drop-down menu 1008, the distance drop-down menu 1010, and/or the address input boxes 1012. Activation of the cancel button 1016, in some implementations, closes the user interface 1000.

Once selections have been made within the aspect ratio input box 1006, the category drop-down menu 1008, the distance drop-down menu 1010, and/or the address input boxes 1012, the advertiser can activate a find button 1014 to locate available property regions to bid on. In some implementations, activating the find button 1014 populates the available property pane 1004 with a list of appropriate properties which are available for bidding. For example, the properties listed within the available property pane 1004 are located within the placement region specified by the distance drop-down menu 1010 and the address input boxes 1012. The property region(s) listed within the available property pane 1004 are sized appropriately for an advertisement of the aspect ratio designated within the aspect ratio input box 1006. The property owner associated with each available property accepts advertisements classified within the category selected within the category drop-down menu 1008.

A property preview column 1018 includes thumbnail images of the available properties. In some implementations, the available region of the property is designated visually within the property preview image (e.g., highlighted, outlined, etc.). A location column 1020 provides an address for each available property. The thumbnail images presented within the property preview column 1018 and the addresses presented within the location column 1020, for example, could be located within the property database 114 of the online property management system 104 (as shown in FIG. 1).

A current maximum received bid is presented within the maximum bid column 1022. The maximum received bid, in some implementations, relates to a bid already placed upon the property pictured within the property preview column 1018. In some implementations, the maximum received bid can relate to a bid that an advertiser placed upon a similar property. The maximum received bid value, for example, can be located within the bids database 128 of the online property management system 104 (as shown in FIG. 1). A bid column 1024 provides the advertiser with a method to input a new bid value for a property. When the advertiser activates a bid button 1026 associated with a listed property, either the bid entered into the bid column 1024 or, if no new bid has been entered, the maximum received bid presented within the maximum bid column 1022, is associated with the advertiser for the property described by the property preview column 1018 and the location column 1020. The advertiser's bid, for example, can be entered within the bids database 128 of the online property management system 104 upon activation of the bid button 1026.

In some implementations, the advertiser can continue to place bids for each desired location presented within the available property pane 1004. Additional information regarding the property, for example the available dates for the auctioned property region, is available in some implementations by selecting (e.g., click on, mouse-over, etc.) the image presented within the property preview column 1018. Additional properties listed within the available property pane 1004 can be accessed by using a scroll bar 1028.

Figure 11:
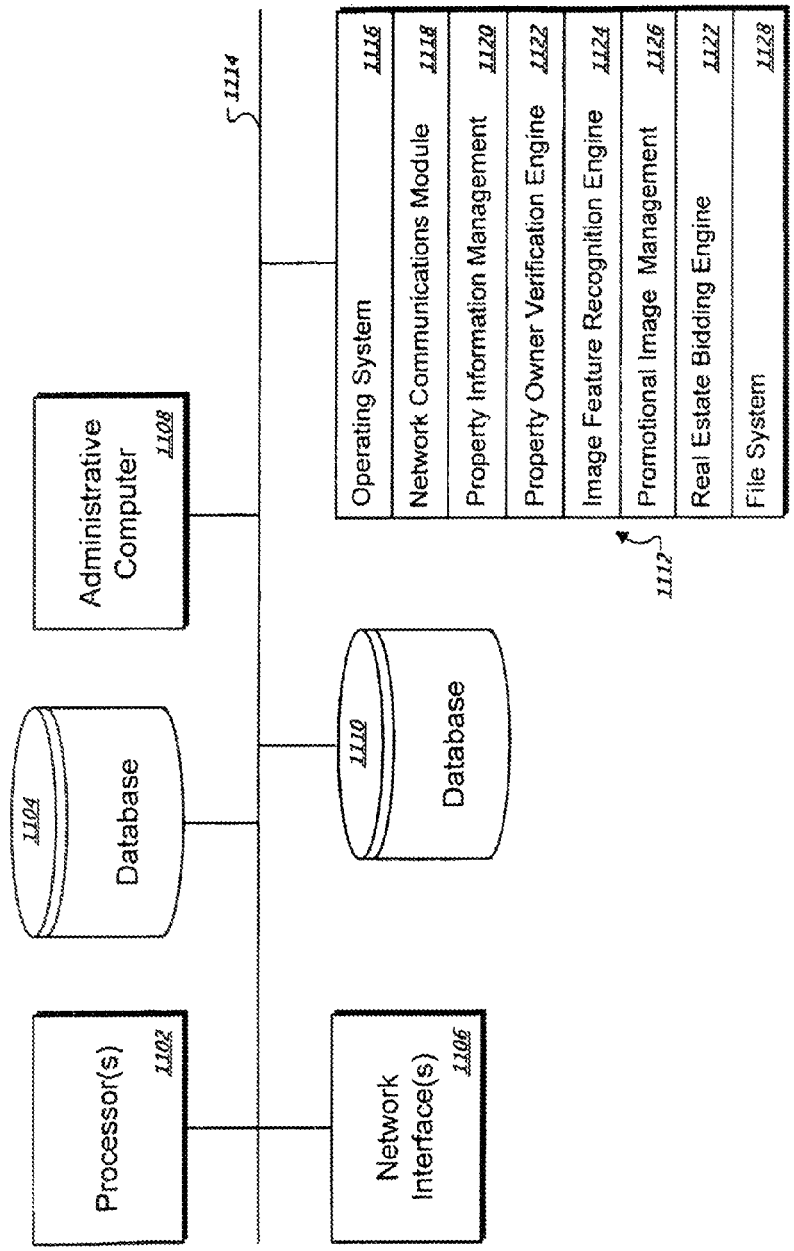
FIG. 11 is a block diagram illustrating an example system architecture for managing advertisements in online three-dimensional or panoramic real estate.

FIG. 11 is a block diagram illustrating an example system architecture 1100 for managing advertisements within online three-dimensional or panoramic real estate. The system architecture 1100 includes one or more processors 1102, one or more network or communication interfaces 1106, databases 1104 and 1110, an administrative computer 1108, memory 1112, and a data bus 1114 interconnecting these components.

The administrative computer 1108 may include input devices, such as a keyboard and mouse, and output devices, such as a display (not shown). From the administrative computer 1108, an administrative computer may administer the online property management system.

Databases 1104 and 1110 may store advertising data and real estate image data, respectively. The advertising data includes information associated with properties, such as the type of property, the location of the property, business information, current promotions, and so forth. The real estate image data can include panoramic or 3-D images of real estate (e.g., city blocks, traffic views, etc.) along with data identifying regions of interest within the image data and data identifying the location (e.g., address, GPS location) of each respective real estate image.

Memory or computer readable medium 1112 may store an operating system 1116 for performing system functions, a network communication module 1118 for communicating with other computers or devices through one or more networks, a property information management engine 1120 for collecting and maintaining advertisement information for various properties, a property owner verification engine 1122 for validating the owners of each property included within the real estate image database 1110, an image feature recognition engine 1124 for identifying the boundaries of individual properties and promotional features within a property, a promotional image management engine 1126 for accepting and coordinating promotional images to overlay upon the real estate images, a real estate bidding engine 1127 for managing regions of interest within the real estate images for advertisement placement, and interfacing with advertisers and property owners to provide bidding opportunities for those regions of interest, and a file system 1128 for storing advertising data, property data, and bidding data pending further processing.

Figure 12:
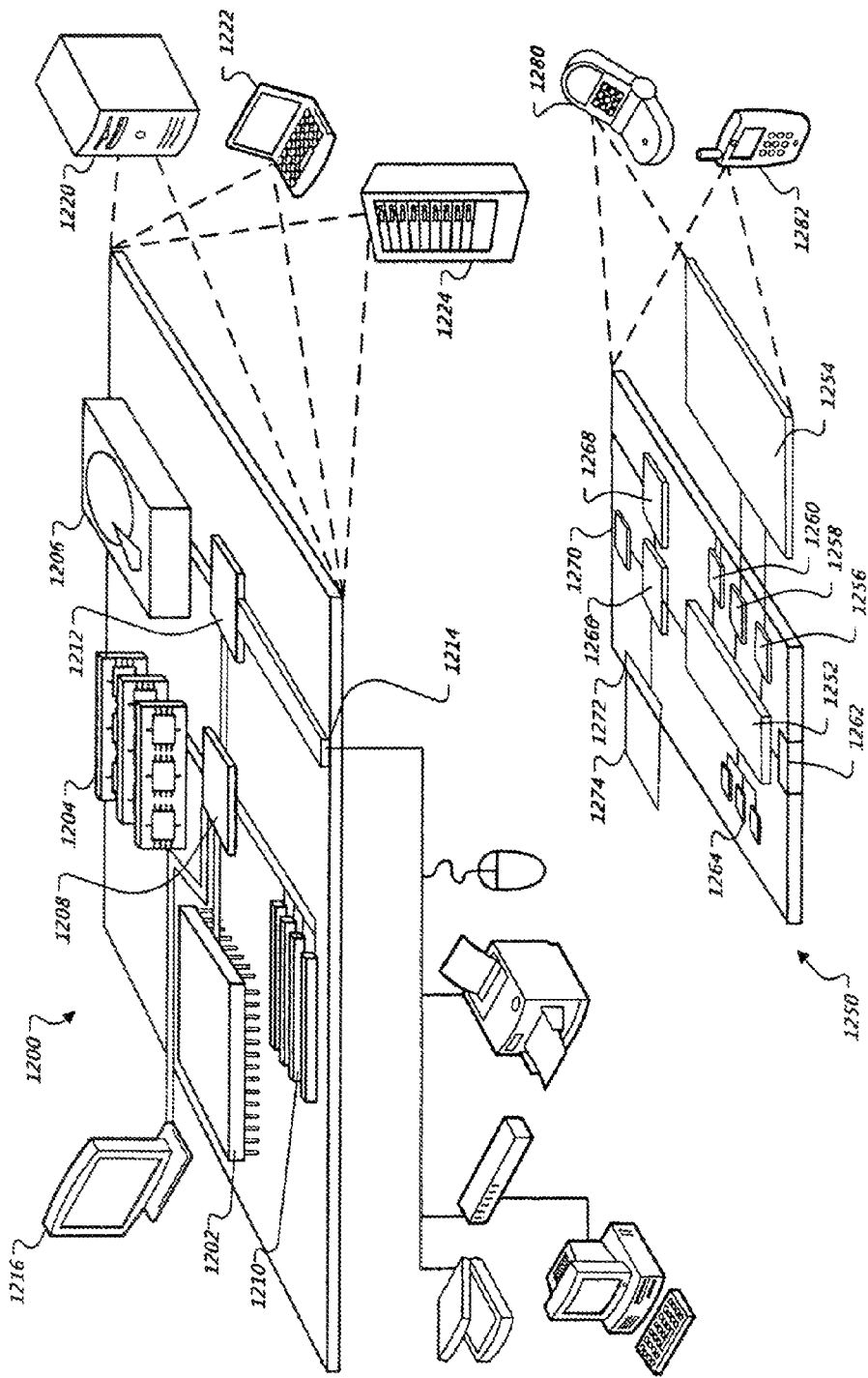
FIG. 12 is an example of a generic computer device and a generic mobile computer device.

FIG. 12 shows an example of a generic computer device 1200 and a generic mobile computer device 1250, which may be used with the techniques described above. Computing device 1200 is intended to represent various forms of digital computers, such as laptops, desktops, workstations, personal digital assistants, television set-top boxes, servers, blade servers, mainframes, and other appropriate computers. Computing device 1250 is intended to represent various forms of mobile devices, such as personal digital assistants, cellular telephones, smartphones, and other similar computing devices. The components shown here, their connections and relationships, and their functions, are meant to be exemplary only, and are not meant to limit the implementations described and/or the claims.

Computing device 1200 includes a processor 1202, memory 1204, a storage device 1206, a high-speed interface 1208 connecting to memory 1204 and high-speed expansion ports 1210, and a low speed interface 1212 connecting to low speed bus 1214 and storage device 1206. Each of the components 1202, 1204, 1206, 1208, 1210, and 1212, are interconnected using various buses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as display 1216 coupled to high speed interface 1208. In other implementations, multiple processors and/or multiple buses may be used, as appropriate, along with multiple memories and types of memory. Also, multiple computing devices 1200 may be connected, with each device providing portions of the necessary operations (e.g., as a server bank, a group of blade servers, or a multi-processor system).

The memory 1204 stores information within the computing device 1200. In one implementation, the memory 1204 is a volatile memory unit or units. In another implementation, the memory 1204 is a non-volatile memory unit or units. The memory 1204 may also be another form of computer-readable medium, such as a magnetic or optical disk.

The storage device 1206 is capable of providing mass storage for the computing device 1200. In one implementation, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1204, the storage device 1206, memory on processor 1202, or a propagated signal.

The high speed controller 1208 manages bandwidth-intensive operations for the computing device 1200, while the low speed controller 1212 manages lower bandwidth-intensive operations. Such allocation of functions is exemplary only. In one implementation, the high-speed controller 1208 is coupled to memory 1204, display 1216 (e.g., through a graphics processor or accelerator), and to high-speed expansion ports 1210, which may accept various expansion cards (not shown). In the implementation, low-speed controller 1212 is coupled to storage device 1206 and low-speed expansion port 1214. The low-speed expansion port, which may include various communication ports (e.g., USB, Bluetooth, Ethernet, wireless Ethernet) may be coupled to one or more input/output devices, such as a pointing device 1230, a printer 1232, a keyboard 1234, a scanner 1236, or a networking device 1237 such as a switch or router, e.g., through a network adapter.

The computing device 1200 may be implemented in a number of different forms, as shown in the figure. For example, it may be implemented as a standard server 1220, or multiple times in a group of such servers. It may also be implemented as part of a rack server system 1224. In addition, it may be implemented in a personal computer such as a laptop computer 1222. Alternatively, components from computing device 1200 may be combined with other components in a mobile device (not shown), such as device 1250. Each of such devices may contain one or more of computing device 1200, 1250, and an entire system may be made up of multiple computing devices 1200, 1250 communicating with each other.

Computing device 1250 includes a processor 1252, memory 1264, an input/output device such as a display 1254, a communication interface 1266, and a transceiver 1268, among other components. The device 1250 may also be provided with a storage device, such as a microdrive or other device, to provide additional storage. Each of the components 1250, 1252, 1264, 1254, 1266, and 1268, are interconnected using various buses, and several of the components may be mounted on a common motherboard or in other manners as appropriate.

The processor 1252 can execute instructions within the computing device 1250, including instructions stored in the memory 1264. The processor may be implemented as a chipset of chips that include separate and multiple analog and digital processors. The processor may provide, for example, for coordination of the other components of the device 1250, such as control of user interfaces, applications run by device 1250, and wireless communication by device 1250.

Processor 1252 may communicate with a user through control interface 1258 and display interface 1256 coupled to a display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may be provide in communication with processor 1252, so as to enable near area communication of device 1250 with other devices. External interface 1262 may provide, for example, for wired communication in some implementations, or for wireless communication in other implementations, and multiple interfaces may also be used.

The memory 1264 stores information within the computing device 1250. The memory 1264 can be implemented as one or more of a computer-readable medium or media, a volatile memory unit or units, or a non-volatile memory unit or units. Expansion memory 1274 may also be provided and connected to device 1250 through expansion interface 1272, which may include, for example, a SIMM (Single In Line Memory Module) card interface. Such expansion memory 1274 may provide extra storage space for device 1250, or may also store applications or other information for device 1250. Specifically, expansion memory 1274 may include instructions to carry out or supplement the processes described above, and may include secure information also. Thus, for example, expansion memory 1274 may be provide as a security module for device 1250, and may be programmed with instructions that permit secure use of device 1250. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1264, expansion memory 1274, memory on processor 1252, or a propagated signal that may be received, for example, over transceiver 1268 or external interface 1262.

Device 1250 may communicate wirelessly through communication interface 1266, which may include digital signal processing circuitry where necessary. Communication interface 1266 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1268. In addition, short-range communication may occur, such as using a Bluetooth, WiFi, or other such transceiver (not shown). In addition, GPS (Global Positioning System) receiver module 1270 may provide additional navigation- and location-related wireless data to device 1250, which may be used as appropriate by applications running on device 1250.

Device 1250 may also communicate audibly using audio codec 1260, which may receive spoken information from a user and convert it to usable digital information. Audio codec 1260 may likewise generate audible sound for a user, such as through a speaker, e.g., in a handset of device 1250. Such sound may include sound from voice telephone calls, may include recorded sound (e.g., voice messages, music files, etc.) and may also include sound generated by applications operating on device 1250.

The computing device 1250 may be implemented in a number of different forms, as shown in the figure. For example, it may be implemented as a cellular telephone 1280. It may also be implemented as part of a smartphone 1282, personal digital assistant, or other similar mobile device.

The disclosed and other implementations and the functional operations described in this description can be implemented in digital electronic circuitry, or in computer software, firmware, or hardware, including the structures disclosed in this specification and their structural equivalents, or in combinations of one or more of them. The disclosed and other implementations can be implemented as one or more computer program products, i.e., one or more modules of computer program instructions encoded on a computer-readable medium for execution by, or to control the operation of, data processing apparatus. The computer-readable medium can be a machine-readable storage device, a machine-readable storage substrate, a memory device, a composition of matter effecting a machine-readable propagated signal, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this description can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, the disclosed techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The disclosed techniques can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of what is disclosed here, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this description contains many specifics, these should not be construed as limitations on the scope of what being claims or of what may be claimed, but rather as descriptions of features specific to particular implementations. Certain features that are described in this description in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understand as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations have been described. Other implementations are within the scope of the following claims.

What is claimed is:

1. A computer-implemented method comprising:
   receiving, by one or more computers, data identifying a region of interest within an image of real property that an agent associated with the real property has designated as available for public bidding;
   determining that a panoramic, geographic view that is obtained in response to a user request includes the region of interest;
   facilitating a bid-based advertisement selection process for the region of interest;
   modifying the panoramic, geographic view to include at least a portion of an image submitted by a winner of the bid-based advertisement selection process; and
   sending code that includes instructions for displaying, on a client device, the panoramic, geographic view on a display of the client device.

2. The computer-implemented method of claim 1, wherein the panoramic, geographic view comprises a street-level image.

3. The computer-implemented method of claim 1, wherein modifying the panoramic, geographic view to include at least a portion of an image submitted by a winner of the bid-based advertisement selection process comprises overlaying the at least the portion of the image submitted by the winner over the a portion of the panoramic, geographic view that corresponds to the region of interest.

4. The computer-implemented method of claim 1, wherein the user request includes an address associated with the real property.

5. The computer-implemented method of claim 1, comprising validating that the agent is associated with the real property before receiving the data identifying the region of interest.

6. The computer-implemented method of claim 1, wherein the agent comprises an owner or occupant of the property.

7. The computer-implemented method of claim 1, further comprising receiving data for altering at least one of a behavior or an appearance of the region of interest from a winner of the bid-based advertisement selection process.

8. A system comprising:
   one or more computers and one or more storage devices storing instructions that are operable, when executed by the one or more computers, to cause the one or more computers to perform operations comprising:
   receiving, by one or more computers, data identifying a region of interest within an image of real property that an agent associated with the real property has designated as available for public bidding;
   determining that a panoramic, geographic view that is obtained in response to a user request includes the region of interest;
   facilitating a bid-based advertisement selection process for the region of interest;
   modifying the panoramic, geographic view to include at least a portion of an image submitted by a winner of the bid-based advertisement selection process; and
   sending code that includes instructions for displaying, on a client device, the panoramic, geographic view on a display of the client device.

9. The system of claim 8, wherein the panoramic, geographic view comprises a street-level image.

10. The system of claim 8, wherein modifying the panoramic, geographic view to include at least a portion of an image submitted by a winner of the bid-based advertisement selection process comprises overlaying the at least the portion of the image submitted by the winner over the a portion of the panoramic, geographic view that corresponds to the region of interest.

11. The system of claim 8, wherein the user request includes an address associated with the real property.

12. The system of claim 8, comprising validating that the agent is associated with the real property before receiving the data identifying the region of interest.

13. The system of claim 8, wherein the agent comprises an owner or occupant of the property.

14. The system of claim 8, further comprising receiving data for altering at least one of a behavior or an appearance of the region of interest from a winner of the bid-based advertisement selection process.

15. A non-transitory computer-readable medium storing software comprising instructions executable by one or more computers which, upon such execution, cause the one or more computers to perform operations comprising:
   receiving, by one or more computers, data identifying a region of interest within an image of real property that an agent associated with the real property has designated as available for public bidding;
   determining that a panoramic, geographic view that is obtained in response to a user request includes the region of interest;
   facilitating a bid-based advertisement selection process for the region of interest;
   modifying the panoramic, geographic view to include at least a portion of an image submitted by a winner of the bid-based advertisement selection process; and
   sending code that includes instructions for displaying, on a client device, the panoramic, geographic view on a display of the client device.

16. The non-transitory computer-readable medium of claim 15, wherein the panoramic, geographic view comprises a street-level image.

17. The non-transitory computer-readable medium of claim 15, wherein modifying the panoramic, geographic view to include at least a portion of an image submitted by a winner of the bid-based advertisement selection process comprises overlaying the at least the portion of the image submitted by the winner over the a portion of the panoramic, geographic view that corresponds to the region of interest.

18. The non-transitory computer-readable medium of claim 15 wherein the user request includes an address associated with the real property.

19. The non-transitory computer-readable medium of claim 15, comprising validating that the agent is associated with the real property before receiving the data identifying the region of interest.

20. The non-transitory computer-readable medium of claim 15, wherein the agent comprises an owner or occupant of the property.

* * * * *